United States Patent [19]

Leichnitz

[11] 4,230,457
[45] Oct. 28, 1980

[54] APPARATUS AND METHOD FOR MEASURING AEROSOLS AND GASES WITH DETECTOR TUBES

[75] Inventor: Kurt Leichnitz, Gross Grönau, Fed. Rep. of Germany

[73] Assignee: Drägerwerk Aktiengesellschaft, Fed. Rep. of Germany

[21] Appl. No.: 967,854

[22] Filed: Dec. 8, 1978

[30] Foreign Application Priority Data

Dec. 8, 1977 [DE] Fed. Rep. of Germany ....... 2754638

[51] Int. Cl.² ............................................ G01N 31/22
[52] U.S. Cl. .................................. 23/232 R; 422/86; 422/60; 422/61
[58] Field of Search .................. 23/232 R, 230 R; 422/56–59, 86, 87, 60, 61

[56] References Cited

U.S. PATENT DOCUMENTS

| 3,019,342 | 1/1962 | Brooke | 23/232 R |
| 3,399,973 | 9/1968 | Grosskoff | 422/60 |
| 3,977,830 | 8/1976 | Topol | 23/232 |
| 4,022,578 | 5/1977 | Kretsch | 422/60 X |
| 4,066,403 | 1/1978 | Bruschi | 422/57 X |

*Primary Examiner*—Michael S. Marcus
*Attorney, Agent, or Firm*—McGlew and Tuttle

[57] ABSTRACT

A device for measuring gases and aerosols with a detector tube, comprises, a duct or test tube for the passage of a test gas therethrough which includes a forelayer in the duct through which the test gas is passed, and which has a substance which will react with the test gas to form a new gas substance. The gas-permeable forelayer advantageously acts as a filter for the aerosol and comprises a substrate, such as a silica gel or a glass fiber, which is impregnated with a material, such as zinc dust and arsenic trioxide which is saturated with water. The aerosol which contains a sulfuric acid in the gas will react after deposit in the forelayer with the zinc forming a nascent hydrogen which reduces the arsenic trioxide immediately to arsenic hydride. The test tube also contains an indicating layer with a material which is known for producing an indication of the newly formed gaseous substance.

2 Claims, 2 Drawing Figures

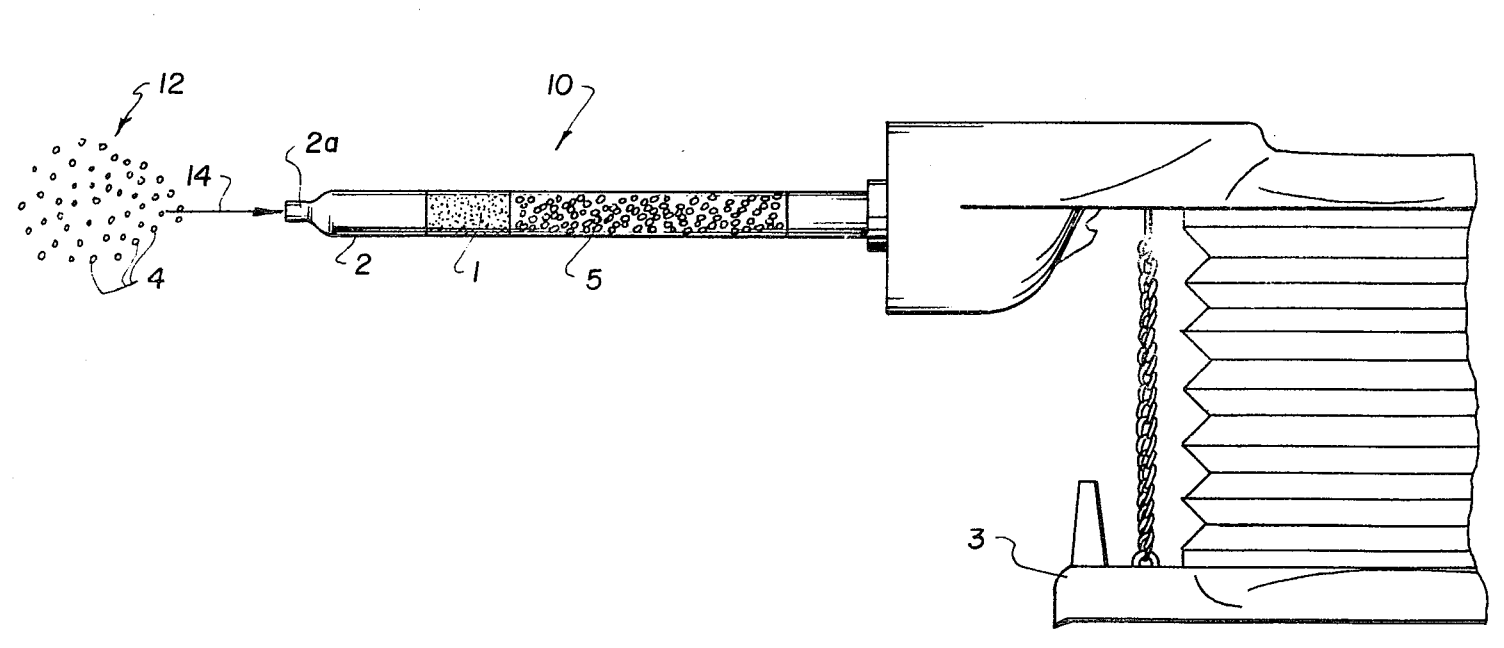

APPARATUS AND METHOD FOR MEASURING AEROSOLS AND GASES WITH DETECTOR TUBES

FIELD AND BACKGROUND OF THE INVENTION

This invention relates to devices for testing gases in general and, in particular, to a new and useful device for measuring gases and aerosols with detector tubes.

DESCRIPTION OF THE PRIOR ART

Test tubes for the quantitative determination of aerosols mixed with gases and/or vapors are not known at the present time. The reason for this lies in the ambiguous reaction behavior of the aerosols in the indicating preparations of the test tubes.

A known method for detecting both volatile and misty arsine war gases uses a test tube in which a filter of inorganic or organic fibrous materials, for example, glass wadding, cellwool or asbestos, is arranged in front of a highly active silica gel layer. When an air sample is passed through, the arsine mists contained therein are retained in the filter, while volative arsines are fixed by the silica gel. Subsequently, a reagent in the form of a solution of tin-(2)-chloride, in concentrated hydrochloric acid is introduced into the test tube.

The mist particles retained by the fiber filter are carried along by the reagent and flushed to the silica gel layer. They react with the reagent only on the silica gel layer. The reaction is thus always in the form of an arsenic deposit on the silica gel in the silica gel layer regardless of whether arsine mist or volatile compounds are present. The reaction takes place directly between the substances to be detected and the indicating reagent. The activity of the silica gel plays a substantial role in the reaction processes. It is greatly influenced by the liquid reagent. This measuring method can therefore only provide qualitative proof of the arsine war gases. Beyond that, the application of the liquid reaction solution is not without risk. (See German Pat. No. 742,689.)

SUMMARY OF THE INVENTION

The present invention is based on the problem of obtaining a quantitative indication in the measurement of aerosols together with simultaneously occurring gases, and/or vapors, bypassing the known difficulties with the ambiguous reaction behavior of the aerosols in the indicating preparations.

According to the invention, the test tube has a forelayer, with an indicating layer arranged behind it in the direction of flow of the gas to be measured. According to a simple solution of the invention, the forelayer is impregnated with an activatable reagent system. The aerosol is deposited in the forelayer by the filter action of the material of the forelayer. After this deposit, it reacts with the reagent system to form a highly volatile reaction product.

The reagent system is now present in excess relative to the aerosol in a stoichiometric consideration of the reaction. The amount of the mass of the highly volative reaction product newly formed in the forelayer, which is completely new with regard to the aerosols and is formed only from the reaction system, is proportional to the mass of the aerosol deposited in the forelayer. The highly volatile reaction product flows toward the following indicating layer where it is measured in a known manner by color reaction. This arrangement ensures a reliable and exact measurement of the aerosol.

The special advantage of the arrangement is that it permits measurement of not only aerosols, but also of gases and vapors. This includes gases and vapors which tend to form aerosols in humid air, e.g., hydrogen chloride, hydrogen fluoride, phosgene, aresenic trichloride and benzyl chloride. Naturally, gaseous products, such as sulfur dioxide, nitrogen dioxide, cyanogen chloride and formic acid can also be reacted.

Accordingly, an object of the invention is to provide a device for measuring gases and aerosols with detector tubes, which comprises, a duct for the passage of a test gas therethrough with a forelayer in the duct through which the test gas is passed, which has a substance which will react with the test gas to form a new gas substance and including an indicating layer arranged in the duct behind the forelayer which will be of a substance to provide an indication of the new gas substance passing therethrough.

A further object of the invention is to provide a method in which the gas to be tested is passed through a first layer so as to cause the gas to react to form a new substance whose characteristics may be clearly indicated by known gas indicating substances and, thereafter, the new substance is passed through the known indicator to obtain an indication of the newly formed substance.

Another object of the invention is to provide a device for measuring gases and vapors which tend to form aerosols in humid air which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a schematic view, partly in section, of a testing device for measuring gases and aerosols with detector tubes, constructed in accordance with the invention.

DESCRIPTION OF THE PREFERRED EMBODIMENT

Referring to the drawing in particular, the invention embodied therein, comprises, a device for measuring gases and aerosols with detector tubes, which includes a known type duct 10 for the passage of a test gas 12 having components indicated at 4 in the only FIGURE of the drawing.

In accordance with the invention, the test tube, made of glass, is filled with a gas-permeable forelayer 1 and a known indicating layer 5 following the forelayer which is of a type which will have a color indication for showing the presence of various types of gases. The glass test tube 2 is of a type in which the forward end or tip 2a is manufactured closed, but can be broken off to open it, as shown in the drawing. The forelayer 1 is arranged ahead of the indicating layer in respect to the direction of flow of the gas to be measured, as indicated by the arrow 14.

The gas specimen to be measured, which contains an $H_2SO_4$ aerosol, is pumped by pump 3 through the glass tube, which is now open after its tip has been broken off. The gas-permeable forelayer 1, acting as a filter for the aerosols, consists of a substrate, such as a silica gel, glass fibers, etc., and is impregnated with zinc dust, as well as arsenic trioxide, and is saturated with water. the $H_2SO_4$ aerosol contained in the gas specimen reacts after the deposit in forelayer 1 (equation 1) with the zinc forming nascent hydrogen (equation 2), which reduces the arsenic trioxide immediately to arsenic hydride (equation 3). The arsenic hydride as a gaseous reaction product reacts then in the following indicating layer 5 with the reagent gold chloride which is already known for test tubes. The amount of the reaction product is then measured.

The chemical process takes place as follows:

1. sorption $H_2SO_4$+forelayer 1 with the impregnation $Zn+As_2O_3+H_2O$,
2. activation in forelayer 1 $Zn+H_2SO_4$ forms $ZnSO_4+2$ [H], hence
3. reduction of $As_2O_3+12$ [H]$=2AsH_3+3H_2O$ in forelayer 1,
4. measurement in indicating layer 5 over the reaction product $AsH_3+AuCl_3=Au+AsCl_3$.

Other combinations of other reagent systems can also be used in forelayer 1, instead of arsenic trioxide and zinc. For example, small quantities of acids are already sufficient to form with cyanides hydrogen cyanide. If these cyanides are reacted with the above-mentioned aerosols or gases and vapors, hydrogen cyanide is formed, which can be easily measured. If sulfides, sulfites or hypochlorites are used in forelayer 1, highly volative and easily measurable reaction products are likewise formed. If forelayer 1 is impregnated with ammonium chloride, we obtain a system which reacts with metal hydroxides, e.g., NaOH, in aerosol form. In this reaction, $NH_3$ is released, which can be easily measured in the following indicating layer 5.

While a specific embodiment of the invention has been shown and described in detail to illustrate the application of the principles of the invention, it will be understood that the invention may be embodied otherwise without departing from such principles.

What is claimed is:

1. A device for measuring $H_2SO_4$ aerosols comprising, means defining a transparent duct for the passage of the aerosols, means defining a forelayer of a gas permeable substrate in said duct through which the aerosols are passed comprising a substance which will react with the aerosols to form a new gas substance, and means defining an additional substrate layer disposed after the forelayer in respect to the direction of gas flow comprising a known indicating substance which will indicate the presence of the new gas substance, said forelayer impregnated with zinc dust, arsenic trioxide and water, and said indicating layer impregnated with gold chloride.

2. A method of measuring $H_2SO_4$ aerosols comprising, passing $H_2SO_4$ aerosols through a forelayer formed of a substrate impregnated with a zinc dust, arsenic trioxide and water, reacting the $H_2SO_4$ aerosols with the impregnated compounds to form a new gas substance, and passing the new gas substance through an indicating layer comprising a gold chloride to obtain a known indication of the presence of the new gas substance.

* * * * *